(12) United States Patent
Simons et al.

(10) Patent No.: US 11,000,817 B2
(45) Date of Patent: May 11, 2021

(54) UREA GRANULATION DEVICE

(71) Applicant: STAMICARBON B.V., Sittard (NL)

(72) Inventors: Petrus Anna Maria Robertus Simons, Schimmert (NL); Johannes Lambertus Kursten, Weert (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 16/961,481

(22) PCT Filed: Dec. 18, 2019

(86) PCT No.: PCT/NL2019/050848
§ 371 (c)(1),
(2) Date: Jul. 10, 2020

(87) PCT Pub. No.: WO2020/130814
PCT Pub. Date: Jun. 25, 2020

(65) Prior Publication Data
US 2020/0376453 A1 Dec. 3, 2020

(30) Foreign Application Priority Data

Dec. 18, 2018 (EP) .................................... 18213505

(51) Int. Cl.
| | | |
|---|---|---|
| *B01J 2/16* | (2006.01) | |
| *C05G 5/12* | (2020.01) | |
| *C05C 9/00* | (2006.01) | |
| *C07C 273/02* | (2006.01) | |
| *B05B 7/04* | (2006.01) | |
| *B01J 8/18* | (2006.01) | |
| *B01J 8/24* | (2006.01) | |

(Continued)

(52) U.S. Cl.
CPC ............... *B01J 2/16* (2013.01); *B01J 8/1827* (2013.01); *B01J 8/245* (2013.01); *B01J 19/26* (2013.01); *B05B 7/0458* (2013.01); *B05B 7/0475* (2013.01); *B05B 7/10* (2013.01); *C05C 9/005* (2013.01); *C05G 5/12* (2020.02); *C07C 273/02* (2013.01)

(58) Field of Classification Search
None
See application file for complete search history.

(56) References Cited

U.S. PATENT DOCUMENTS 3,631,608 A * 1/1972 Maresca ................ B01J 8/1818
   34/364
3,887,337 A * 6/1975 Descamps ............... B01J 8/386
   422/143

(Continued)

FOREIGN PATENT DOCUMENTS

DE         10146778 A1    4/2003

OTHER PUBLICATIONS

Stamicarbon B.V., Launch Finish Granulation Design, Brochure, Nov. 2016, 3 pages.

(Continued)

*Primary Examiner* — Wayne A Langel
(74) *Attorney, Agent, or Firm* — Leason Ellis LLP (57) ABSTRACT

A fluidized bed granulator for granulation with urea or urea-containing liquids is described, wherein the granulation liquid is supplied via a supply manifold comprising a header and risers. The risers are at least in part provided inside channels for secondary gas.

14 Claims, 4 Drawing Sheets

(51) Int. Cl.
 *B01J 19/26* (2006.01)
 *B05B 7/10* (2006.01)

(56) References Cited

U.S. PATENT DOCUMENTS

| | | |
|---|---|---|
| 5,395,449 A | 3/1995 | Quadir et al. |
| 5,964,901 A | 10/1999 | Kido et al. |
| 6,203,730 B1 | 3/2001 | Honda et al. |
| 2012/0282361 A1 | 11/2012 | Kojima et al. |

OTHER PUBLICATIONS

"Coming of Age" In Nitrogen & Methanol, No. 272, Nov.-Dec. 2004, pp. 37-43, XP001212587.
International Search Report and Written Opinion in corresponding International Patent Application No. PCT/NL2019/050848, dated Mar. 23, 2020.

\* cited by examiner

UREA GRANULATION DEVICE

CROSS-REFERENCE TO RELATED PATENT APPLICATIONS

This application is a U.S. National Stage Application under 35 U.S.C. § 371 of International Patent Application No. PCT/NL2019/050848, filed Dec. 18, 2019, which claims the benefit of priority under 35 U.S.C. § 119 of European Patent Application number 18213505.3 filed Dec. 18, 2018, both of which are incorporated by reference in their entireties. The International Application was published on Jun. 25, 2020, as International Publication No. WO 2020/130814 A1.

INTRODUCTION

The invention pertains to a fluidized bed granulator. The granulator is in particular suitable for granulation with urea or urea-containing liquids, such as urea melt. The granulator is for instance suitable for forming urea or urea-containing granules. Urea granules (which may include additives such as ammonium salts) are used mainly as fertilizer and can e.g. also be used for cattle feed and for $NO_x$ abatement.

The invention pertains to a fluidized bed granulator. In operation of such a granulator, a fluidized bed of particles is maintained in one or more granulation compartments by supplying fluidization gas, often air, through a fluidization plate. This plate is arranged at the bottom of said compartments and has numerous openings for fluidization gas. In operation of the device, granulation liquid (e.g. urea melt, such as with more than 90 wt. % or more than 95 wt. % urea, e.g. with less than 5 wt. % water) is supplied into the fluidized bed using nozzles in the fluidization plate. The nozzles also use secondary gas, often air, which gas is for example used in the nozzles for atomization of the granulation liquid into a spray or for transport of the particles through a film of the granulation liquid, which film is formed by the nozzle. In each granulator compartment, the nozzles are typically provided in an array in the fluidization plate. In operation, the fluidization gas goes up through the openings in the fluidization plate, to ensure the fluidization of the particles in the granulation compartments and to take away crystallization heat. Hence, below the fluidization plate, three supply systems are arranged: a fluidization gas supply system, a granulation liquid supply system (e.g. for urea melt), and a secondary gas supply system.

In the present invention, the fluidization gas and the secondary gas are supplied separately, e.g. at different temperatures, different flow rates and/or different pressures, and are for example both air. In a preferred embodiment, the fluidization gas temperature is up to 50° C. (minimum temperature is for example ambient temperature) and the secondary gas has a temperature of for example at least 60° C. or at least 100° C., and for example up to 150° C. In the invention, the preferred high temperature of the secondary gas, preferably secondary air, can be advantageously be used for preventing a urea melt as preferred granulation liquid from solidifying in parts of the granulation liquid supply manifold of the granulator according to the invention that are located within the space for secondary gas.

EP 2055373 (also published as US 2012/0282361) describes a granulator comprising a granulation unit having a bottom floor with a perforated plate at its bottom part, an upper air-supplying pipe for supplying fluidization air to the bottom floor, and spray nozzles for spraying the granulation liquid. The nozzles are provided in the centre of air outlets of air-supplying pipes which are each branched off from a lower air-supplying pipe and which pipes have each an opening in the bottom floor for jetting the air into the granulation unit. EP 2055373 illustrates in FIG. 1 schematically a granulator with spray nozzles connected to a horizontal granulation supply line which passes extensively through an upper air-supplying pipe for fluidization air. In EP 2055373, fluidization air is at 44° C. and thus relatively cold (Table 2), such that there is a risk of cooling and solidification of the granulation liquid in the header in EP 2055373, or alternatively the granulation liquid must be very warm at the inlet of the granulator of EP 2055373.

The document "STAMI UREA LAUNCH FINISH Granulation Design" describes that in the Stamicarbon urea granulation technology, a fluid bed granulator is used wherein urea melt is introduced via multiple film spray nozzles. A continuous stream of secondary air is introduced via the air ring installed around each spray nozzle and takes care of the transport of the seeds/granules through the urea melt-film. The fluid bed granulator is divided into multiple granulation sections in which urea melt is introduced via nozzles and some cooling sections in which the formed granules are cooled down. Fluidization air is distributed over the granulation and cooling sections to maintain the fluidized bed and to take away the generated crystallization heat.

The article "Coming of age" in Nitrogen & Methanol no. 272, November-December 2004, pages 37-43, XP001212587, mentions that the granulator of the Stamicarbon fluidized-bed urea granulation process includes a number of header manifolds along the granulator. These headers are located below the fluidization plate and each comprises an air header tube with a coaxial melt header tube inside the air header tube.

An object of the present invention is to provide an improved fluidized bed granulator.

SUMMARY

The invention relates in a first aspect to a fluidized bed granulator for granulation with urea or urea-containing liquids, the granulator comprising a granulator enclosure, wherein the granulator enclosure comprises: a lower wall, an upper wall, an inlet for fluidization gas, an inlet for secondary gas, an outlet for solid product particles, an outlet for exhaust gas, and optionally an inlet for seed particles, wherein the granulator enclosure comprises a plurality of granulation compartments, which are arranged in series in a length direction of the granulator, wherein the granulator further comprises an inlet for granulation liquid and a granulation liquid supply manifold, wherein the granulation liquid supply manifold comprises a granulation liquid header and a plurality of risers, wherein the granulation liquid header is connected to said inlet for granulation liquid and to a plurality of said risers, wherein the granulator enclosure further comprises a fluidization plate and at least in said granulation compartments a separation plate, wherein the separation plate is spaced apart from the fluidization plate in vertical direction and is placed below the fluidization plate, wherein the separation plate is arranged between said lower wall and said fluidization plate, wherein said granulator enclosure comprises a first space between said upper wall and said fluidization plate, a second space between said fluidization plate and said separation plate, and a third space between said separation plate and said lower wall, said first, second and third space each having an enclosure, wherein said granulator is configured for holding a fluidized bed of particles in operation in said first space, and wherein the enclosure of said first space comprises said outlet for solid product particles, said outlet for exhaust gas, and optionally said inlet for seed particles, wherein the enclosure of said second space comprises said inlet for fluidization gas, and wherein the fluidization plate comprises openings for passage of said fluidization gas from said second space to said first space, wherein said enclosure of said third space comprises said inlet for secondary gas, wherein the granulator comprises in said granulator compartments a plurality of nozzles for supplying said granulation liquid into said first space, wherein at least one of said nozzles comprises a nozzle inlet for said secondary gas and a nozzle inlet for said granulation liquid, wherein said granulator comprises a secondary gas channel which extends from a secondary gas opening in said separation plate through said second space to said nozzle inlet for secondary gas, wherein said granulation liquid supply manifold is in part provided in said third space and in part in said second space and wherein at least one of said risers is at least in part provided inside said secondary gas channel, wherein said riser passes through said secondary gas opening or is joined to said header at said secondary gas opening.

The invention also pertains to a urea granulation method, carried out in such a granulator, wherein the method comprises supplying urea melt as granulation liquid to the inlet for granulation liquid and through the granulation liquid supply manifold including the header and the risers, supplying fluidization gas to the inlet for fluidization gas and supplying secondary gas to the inlet for secondary gas of the granulator, and withdrawing granulate from the granulate outlet, and maintaining a fluidized bed of granules in the first space and supplying granulation liquid into the first space using the nozzle.

BRIEF DESCRIPTION OF THE DRAWINGS

FIG. 2 schematically illustrates an example granulator according to the invention; wherein

FIG. 6 schematically illustrates granulators.

DETAILED DESCRIPTION

The granulator of the invention has a special configuration of the spaces used for the supply of fluidization gas and of secondary gas to the granulator and of the granulation liquid supply manifold. This configuration allows for example for easier cleaning of the granulator. Further advantages of the invention are discussed hereinafter in the detailed description.

A feature of the granulator according to the invention is that it comprises a granulation liquid supply manifold which is in part provided in the third space which comprises an inlet for secondary gas. This provides the advantage that the relatively large volume of relatively hot secondary gas in the third space heats the granulation liquid in said part of the granulation liquid supply manifold.

In a preferred embodiment, the granulation liquid header is provided in the third space and the enclosure of the third space comprises the inlet for granulation liquid. In this preferred embodiment, the header is in particular arranged entirely inside the third space. Advantageously, granulation liquid in the header is in indirect heat exchanging contact with the relatively hot secondary gas in the third space such that heat losses are reduced.

Figure 1:
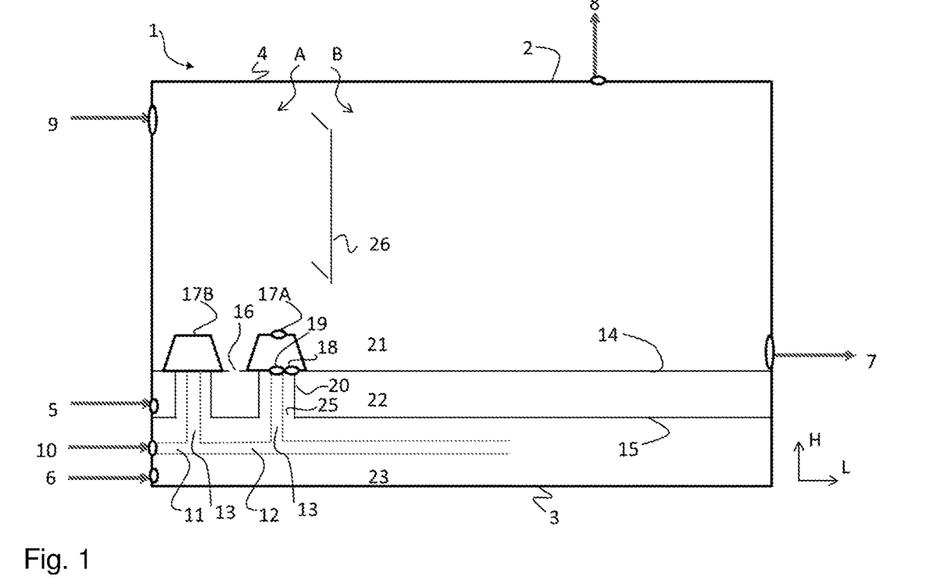
FIG. 1 schematically illustrates an example granulator according to the invention.
Figure 2A:
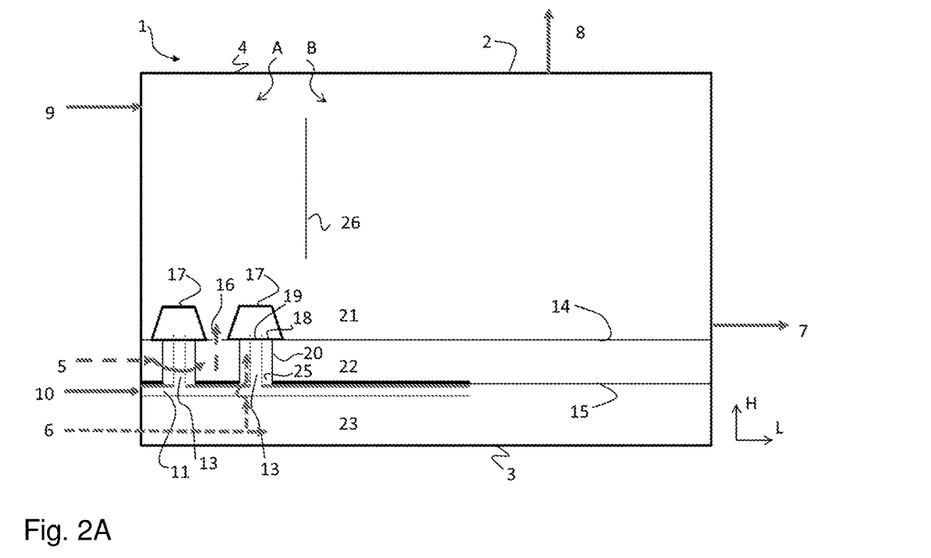
FIG. 2A shows an overview and FIG. 2B shows an enlarged part cross-section.
Figure 2B:
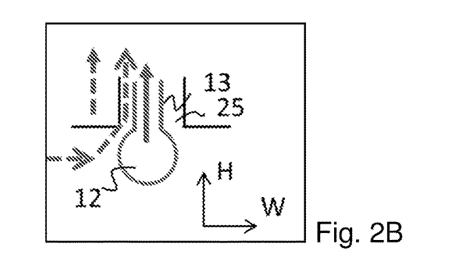
Figure 3:
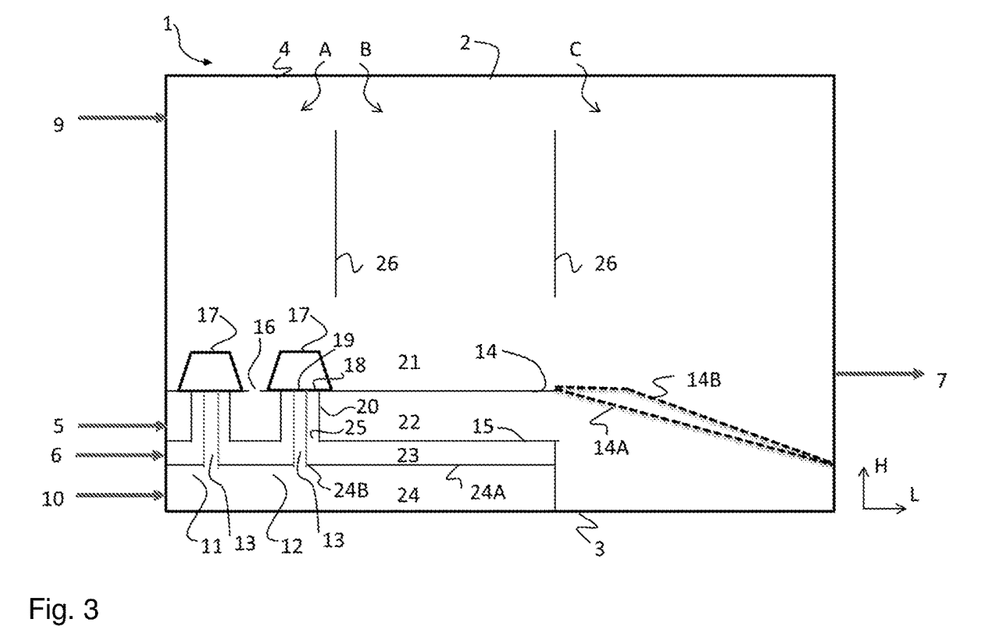
FIG. 3 schematically illustrates an example granulator according to the invention.

An example fluidized bed granulator (1) is illustrated in FIGS. 1, 2 and 3. In the following general discussion, the reference signs to items illustrated in the drawings are given merely for convenience; these reference signs do not limit the invention or the claims.

The invention pertains to a fluidized bed granulator a fluidized bed granulator (1) for granulation with urea or urea-containing liquids. The granulator comprises a granulator enclosure (2). The granulator enclosure (2) comprises a lower wall (3), an upper wall (4), an inlet for fluidization gas (5), an inlet for secondary gas (6), an outlet for solid product particles (7), an outlet for exhaust gas (8), and optionally an inlet for seed particles (9). The granulator enclosure (2) comprises a plurality of granulation compartments (A, B), which are arranged in series in a length direction of the granulator. The granulator (1) further comprises an inlet for granulation liquid (10) and a granulation liquid supply manifold (11). The granulation liquid supply manifold (11) comprises a granulation liquid header (12) and a plurality of risers (13). The granulation liquid header (12) is connected to the inlet for granulation liquid (10) and to a plurality of said risers (13). The granulator enclosure (2) further comprises a fluidization plate (14) and at least in said granulation compartments (A, B) a separation plate (15). The separation plate (15) is spaced apart from the fluidization plate (14) in vertical direction and is placed below the fluidization plate (14). The separation plate (15) is arranged between said lower wall (3) and said fluidization plate (14).

The granulator enclosure (2) furthermore comprises a first space (21) between said upper wall (4) and said fluidization plate (14), a second space (22) between said fluidization plate (14) and said separation plate (15), and a third space (23) between said separation plate (15) and said lower wall (3). Said first, second and third space each has an enclosure. The granulator is configured for holding a fluidized bed of particles in operation in said first space (21). The enclosure of said first space (21) comprises said outlet for solid product particles (7), said outlet for exhaust gas (8), and optionally said inlet for seed particles (9). The enclosure of said second space (22) comprises said inlet for fluidization gas (5). The fluidization plate (14) comprises openings (16) for passage of said fluidization gas from said second space (22) to said first space (21). The enclosure of said third space (23) comprises said inlet (6) for secondary gas.

The granulator furthermore comprises in said granulator compartments (A, B) a plurality of nozzles (17) for supplying said granulation liquid into said first space (21). At least one of said nozzles (17) comprises a nozzle inlet (18) for said secondary gas and a nozzle inlet (19) for said granulation liquid. The granulator comprises a secondary gas channel (20) which extends from a secondary gas opening (25) in said separation plate (15) through said second space (22) to said nozzle inlet (18) for secondary gas. The granulation liquid supply manifold (11) is in part provided in said third space (23) and in part in said second space (22). At least one of said risers (13) is at least in part provided inside said secondary gas channel (20). Said riser (13) passes through said secondary gas opening (25) or is joined to said header (12) at said secondary gas opening (25).

The granulator is in particular suitable for granulation with urea or urea-containing liquids.

The granulator enclosure (2) is often box-shaped, and can also be e.g. oval-shaped in top view. The enclosure is usually oblong, e.g. having a horizontal length direction larger (e.g. at least 2 times larger) than the perpendicular horizontal width direction. The granulator enclosure (2) comprises a lower wall (3), an upper wall (4), and sidewalls. The lower wall is e.g. a metal plate or a concrete floor. The granulator enclosure (2) comprises a first space (21). The granulator enclosure comprises a plurality of granulation compartments (A, B). The granulation compartments are arranged in series in a length direction of the granulator, and are typically provided in said first space (21).

The granulation enclosure (2), in particular the first space (21), furthermore preferably comprises at least one cooling compartment (C) downstream of said granulation compartments. The compartments are separated from each other by a divider such as a baffle (26), the divider is e.g. a plate connected to a side wall and the first space e.g. includes openings between the dividers and the fluidization plate (14) and between the dividers and the top wall, to allow for transport of the particles. The use of a plurality of compartments arranged in series, separated by such dividers, provides for a better controlled residence time of the particles in the granulator. In operation, the particles in the fluidized bed move from the upstream compartment to the downstream compartments, and generally to the granulate outlet (7) where the formed particles are withdrawn. Undersized granules are optionally recycled, e.g. as seeds; oversized granules in the granulate material are optionally crushed (typically outside the granulator) and the crushed granules are e.g. recycled. In some embodiments, the recycle of undersized granules and/or (crushed) oversized granules is omitted.

The granulator (1) further comprises an inlet for granulation liquid (10) and a granulation liquid supply manifold (11). In a urea plant, the inlet is e.g. for urea melt, comprising e.g. at least 90 wt. % or at least 95 wt. % or at least 98 wt. % urea; and typically comprises a granulation additive such as formaldehyde. The melt may also comprise biuret. The granulation liquid may for instance also comprise or essentially consist (e.g. at least 90 wt. %) of a mixture of urea, optionally biuret, and an additive, the additive is for example an ammonium salt. The granulation liquid usually comprises less than 5 wt. % or less than 2 wt. % water.

The granulation method carried out in the granulator is for example based on evaporation of water and/or cooling of the granulation liquid to provide for solidification of granulation liquid and growth of the particles. For example, cooling is provided by the fluidization gas and/or secondary gas. In an example embodiment of the granulation method, a granulation liquid, preferably a urea melt, solidifies in the granulator and in particular on the granules. In example embodiments wherein the nozzles are film-forming spray nozzles, the granulation may involve layered growth of the granules.

The granulation liquid inlet is for instance connected to (an outlet of) an evaporation section of a urea plant, such as to a vacuum evaporation stage or stages.

The granulator, in particular the granulation space, comprises an outlet for exhaust gas (8) (typically in the upper wall or near the top and/or typically at a downstream end in length direction), an outlet for solid product particles (7) and optionally an inlet for seed particles (9). The granulate outlet (7) and the optional seeds inlet (9) are typically at opposite ends of the granulator enclosure (2), the ends are opposite in the length direction of the granulator. The granulate outlet (7) is for instance provided in said cooling compartment (C).

The granulator enclosure (2) furthermore comprises an inlet for fluidization gas (5), and a separate inlet for secondary gas (6). In this way the fluidization gas (e.g. air) and secondary gas (e.g. air) can have different temperatures, flow rates, composition and/or pressure in operation.

The granulator enclosure (2) further comprises a fluidization plate (14). The fluidization plate forms the bottom of the granulation compartments (A, B) and of the optional cooling compartment (C). The fluidization plate (14) comprises openings (16) for passage of the fluidization gas to the first space (21), in particular to the granulation compartments (A, B) and to the optional cooling compartment (C). In this way, the granulator is configured for holding a fluidized bed of particles in operation in said first space (21). The enclosure of the first space (21) comprises the outlet (7) for solid product particles (i.e. the granules), the outlet for exhaust gas (8) (for exhaust gas corresponding to the fluidization gas and the secondary gas), and optionally the inlet for seed particles (9), herein the enclosure of the first space is e.g. provided by the side walls and/or top walls of the granulation compartments (A, B) and optional cooling compartment (C) and the fluidization plate (14). The first space (21) is accordingly arranged between the upper wall (4) and the fluidization plate (14). The fluidization plate (14) is for example arranged as a horizontal plate, and is optionally slightly inclined (e.g. up to 10° or up to 2°), in particular in the length direction.

The separation plate (15) is often arranged as horizontal plate, but can also be slightly inclined (e.g. up to 10° or up to 2°), in particular in the length direction, e.g. with the highest part of the plate nearer to the gas outlet (8) than the lowest part of the plate. This can be used to ease the cleaning, e.g. of insoluble biuret which can be flushed to a lower side of the plate for easy removal. The fluidization plate (14) and the separation plate (15) are often arranged as parallel plates, but can also be slightly inclined to each other, e.g. up to 10° or up to 5°. In case of an inclined separation plate, the fluidization plate is preferably also inclined and parallel to the inclined separation plate to optimize the gas flow.

The granulator comprises in the granulator compartments (A, B) a plurality of nozzles (17) for supplying the granulation liquid into the first space (21). The nozzles are for example film spray nozzles or atomization nozzles, other types of nozzles are also possible in the granulator of the invention. In some embodiments, the granulator compartments comprise a plurality of spouts for supplying the granulation liquid into the first space, for example as the nozzles (17). Preferably, the nozzles extend through an opening in the fluidization plate. Preferably each nozzle has a nozzle outlet for granulation liquid which protrudes from the fluidization plate into the first space. The nozzles are usually provided at intervals in the length direction, these intervals contribute to layered growth. The nozzles are in some embodiments mounted on the fluidization plate, inside the first space. However, preferably each nozzle extends through an opening in the fluidization plate, and each nozzle is for example not wider than the opening at least the spraying end of the nozzle. Advantageously in some embodiments the fluidization plate can easily be removed (e.g. for cleaning purposes) by moving the plate up and the nozzles do not block such movement. The fluidization plate has for instance one opening for each nozzle.

At least one nozzle (17), preferably a plurality of nozzles (e.g. more than 10 or more than 30 nozzles) or even all nozzles, comprises a nozzle inlet (18) for the secondary gas, and further comprises a separate a nozzle inlet (19) for the granulation liquid. The nozzle inlet (18) for the secondary gas is connected to the inlet of the granulator enclosure for secondary gas (6). The nozzle inlet (19) for the granulation liquid is connected to the granulation liquid inlet (10) of the granulator through the granulation liquid supply manifold (11).

In the fluidized bed granulator of the invention, the granulation liquid supply manifold (11) comprises a granulation liquid header (12) and a plurality of risers (13), wherein the granulation liquid header (12) is connected to the inlet for granulation liquid (10) of the granulator and to a plurality of the risers (13).

Furthermore, the granulator enclosure (2) comprises, at least in said granulation compartments (A, B) a separation plate (15). The separation plate (15) is spaced apart from the fluidization plate (14) in vertical direction and is placed below the fluidization plate (14) in the granulator enclosure. Hence, the separation plate (15) is arranged between the lower wall (3) and the fluidization plate (14). In some embodiments, the separation plate (15) is omitted in the cooling compartment (C) (see e.g. FIG. 3).

The granulator enclosure (2) accordingly comprises, in addition to the first space (21), a second space (22) between the fluidization plate (14) and the separation plate (15), and a third space (23) between the separation plate (15) and the lower wall (3). The first, second and third space each have an enclosure (formed by said pair of plates and/or wall, and the sidewalls of the granulator).

Figure 8:
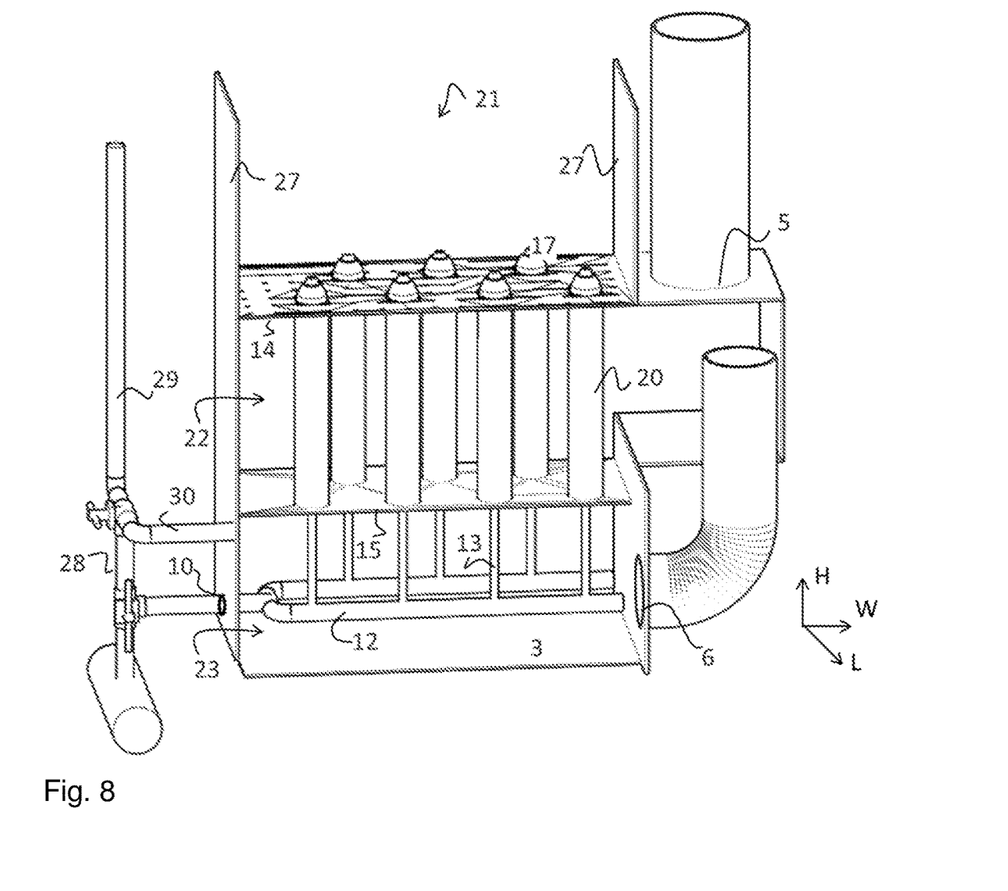
FIG. 8 illustrates an isometric view of an example granulator according to the invention.

The enclosure of the second space (22) comprises the inlet (5) for fluidization gas, e.g. in a sidewall, and in case of a box-shaped granulator, for instance in a long sidewall parallel to the length direction. The enclosure of the third space (23) comprises the inlet (6) for secondary gas, e.g. in a sidewall, and in case of a box-shaped granulator, for instance in a long sidewall parallel to the length direction, as is illustrated in FIG. 8 which shows the side walls (27).

The granulator comprises a secondary gas channel (20) which extends from a secondary gas opening (25) in the separation plate (15) through the second space (22) to a nozzle inlet (18) for secondary gas. In this way, in operation secondary gas enters the granulator enclosure at the inlet (6), flows through the third space (23), through a secondary gas opening (25) and through the secondary gas channel (20) that is connected to said opening (25), and arrives at a nozzle inlet (18) of a nozzle (17). Preferably, the secondary gas channel (20) is arranged as a straight vertical tube connecting a secondary gas opening (25) and a nozzle inlet (18) which are arranged on the same vertical line, e.g. on a straight line at 85° to 95°, or at 90° perpendicular to horizontal or at such angle to the separation plate (15), i.e. with a vertical angle in that range for at least one direction in the horizontal plane.

Furthermore, in operation, fluidization gas enters the granulator enclosure at the fluidization gas inlet (5), flows through the second space (22), and then through one of the numerous openings (16) in the fluidization plate into the first space (21).

In the granulator of the invention, the granulation liquid supply manifold (11) is in part provided in the third space (23), hence below the separation plate (15). This first part contains the inlet for granulation liquid (10), or receives granulation liquid from the granulation liquid inlet (10), and is in particular upstream (for granulation liquid) of the risers (13). The other second part of the granulation liquid supply manifold (11) is provided by the risers (13), which risers (13) are at least in part provided in the second space (22).

In order to span the vertical distance between the part of the granulation liquid supply manifold (11) below the separation plate (15) and the nozzle inlet (19), at least one of said risers (13) (for granulation liquid) is at least in part provided inside a secondary gas channel (20). The riser (13) passes through the secondary gas opening (25) of the secondary gas channel (20), in a less preferred embodiment the riser is joined to the header (12) at this secondary gas opening (25). The riser (13) is at one end (the upper end) connected to a nozzle inlet (19). The secondary gas opening (25) is preferably a bottom opening of the secondary gas channel (20), or the channel (20) is e.g. a tube extending through the opening (25) and having a bottom end inside the third space (23) and below the separation plate (15).

In this way, granulation liquid is supplied at the inlet for granulation liquid (10) into the granulation liquid supply manifold (11), flows through the header (12) and upward through a riser (13) to arrive at a nozzle inlet (19). The riser (13) is e.g. a tube with in operation in the inside granulation liquid and on the outside secondary gas, as the riser is at least in part provided inside a secondary gas channel (20). For example, the riser (13) and the secondary gas channel (20) are concentric tubes. Preferably, the riser tubes are at least as long as the secondary gas tubes, and in some embodiments they are even longer.

Preferably, the riser tubes span at least the vertical distance between the separation plate and the fluidization plate. Preferably, each riser tube is connected to only one nozzle. Preferably, the granulation liquid supply manifold comprises a number of splits (e.g. tube joints) for dividing the granulation liquid into streams going to individual nozzles, and/or for taking a first stream of granulation liquid going to only one nozzle from a second stream of granulation liquid to a plurality of nozzles. An example of such split is the joint between the header and an individual riser, e.g. as shown in FIG. 1. Preferably, at least some of these splits, preferably all of these splits are arranged below the separation plate. Preferably, the tubes or piping for granulation liquid that is arranged in the second space, consists of tubes or piping for granulation liquid streams going to only one nozzle. In some embodiments, these joints or splits for granulation liquid streams to individual nozzles are arranged straight below the granulation liquid inlet of that nozzle, i.e. the nozzle inlet and corresponding split (e.g. tube joint) differ in position only in the vertical direction and not in the length and/or width direction.

The configuration of the granulation liquid supply manifold and the second and third space advantageously provides for a simpler construction than known headers for granulation liquid of granulators. Furthermore, in some embodiments the whole granulation liquid supply manifold can advantageously be provided in the granulator enclosure or granulator casing. This allows for a simpler and lower weight construction of the granulator. The number of wall protrusions (inlets and outlets openings and tubes) can be reduced, thereby reducing the weakening of the granulator walls and avoiding or at least reducing the need for reinforcement structures in the walls.

The configuration is particularly advantageous for the cleaning of the granulator. For cleaning of the granulator, usually first large chunks (solid pieces) are removed from the first space (21). Thereafter the first space (21) is further cleaned with water (or other solvent) to dissolve any remaining solids (e.g. urea). This causes the contaminated water and the urea particles (or other solid particles) to enter the second space (22) through the openings (16) in the fluidization plate (14). With the configuration of the present invention, the second space (22) is much larger and/or much more accessible for cleaning compared to e.g. the prior art granulators identified hereinabove. In particular, the risers (13) are elegantly provided inside the secondary gas channel (20). Hence, in some embodiments the second space (22) advantageously does not contain any equipment parts, other than the secondary gas channels (20), which equipment parts if present would hinder the cleaning or block access to the bottom of the second space (i.e. the separation plate (15)). In contradistinction, in know urea granulators, often a header for urea is provided in the space for fluidization gas, and typically also a supply header for the secondary gas; these headers form obstructions for cleaning.

A further advantage is that since the granulation liquid supply manifold is at least in part provided within the space containing in operation the secondary gas (the third space), which secondary gas is hot, less insulation is necessary to keep the granulation liquid above the solidification temperature upstream of the nozzles; even more so because the risers are shielded by the hot secondary gas in operation.

Furthermore less branching of the supply manifold increases flexibility in placing insulation around the manifold, especially around the risers. In particular, the urea supply manifold is in some attractive embodiments completely embedded in the secondary gas space. This provides the advantage that the urea melt stays at a higher temperature, at a molten state, during the entire transport to the nozzles.

Advantageously, the granulation configuration of the invention allows for the total pressure drop in the system upstream of the nozzles, for the granulation liquid and/or for the secondary gas, to be considerably less than the pressure drop in the spraying nozzles, e.g. of the total pressure drop at least 90%, or even at least 95% is provided in the channels, for the for the granulation liquid and/or for the secondary gas. Such localization of the pressure drop mainly in the nozzles advantageously contributes to a more even distribution of the supplied secondary gas (e.g. air) and/or the granulation liquid, e.g. the urea containing melt.

The configuration of the present invention allows for easy cleaning, for instance manually after removing the fluidization plate. The configuration also allows for using (semi)-automatic cleaning system, for example by spraying a cleaning liquid, such as water, into the second space. Urea deposits are not expected to form inside the secondary gas channel because it is not connected to the second space, but if necessary rinsing of the channels is possible.

In the present invention, the fluidization gas and the secondary gas are supplied separately, e.g. at different temperatures, different flow rates and/or different pressures, and are for example both air. In some embodiments of the invention, the fluidization gas is at a temperature below 70° C., such as 5° C. to 50° C. and the secondary gas is e.g. at above 100° C., such as 140° C. to 150° C. The secondary gas is for instance at least 20° C. or at least 50° C. warmer than the fluidization gas. This provides the advantage of preventing solidification of the granulation liquid, e.g. urea melt, running in the granulation liquid supply manifold (11), in particular in the risers (13).

In a preferred embodiment, the secondary gas channel is a first tube and the riser or part of the riser that is provided in the secondary gas channel is a second tube, wherein the first tube surrounds the second tube, in a cross-section of the tubes in a horizontal plane for at least one vertical position, and preferably all vertical positions of the riser or part of the riser that is provided in the secondary gas channel. The tubes can have any shape in cross section in the horizontal plane, for instance a circle, a polygon (in particular simple polygons such as square, pentagon, and hexagon), or other shapes.

In an example embodiment, the secondary gas channel and the riser (or the part of the riser that is provided in the secondary gas channel), are provided as concentric tubes. Optionally the cross-sections in the horizontal plane of the first and second tube have the same centre for at least one vertical position. Preferably the secondary gas channel is an outer tube, and the riser (or that part of the riser) is an inner tube having a smaller diameter than the outer tube. The outer tube preferably completely surrounds the inner tube in a cross-section in the horizontal plane for at least a part of the length of either tube. An example of such tubes is illustrated in FIG. 1.

In a preferred embodiment, the granulator comprises at least one divider (26) dividing the first space into zones, wherein these zones define the granulation compartments (A, B). The second space is divided or undivided between the granulation compartments, preferably the second space is divided into compartments by separation walls and each compartment has an inlet for fluidization gas. The third space (for secondary gas) is divided or undivided between said granulation compartments. Preferably the third space is divided into compartments by separation walls and each compartment has an inlet for fluidization gas. The optional fourth space (for granulation liquid) is divided or undivided between said compartments. Preferably the optional fourth space is divided into compartments by separation walls and each compartment comprises one or more inlets for granulation liquid. Preferably, said separation walls correspond to the dividers of the first space, such that a granulation compartment has a corresponding compartment of the second space and of the third space, and optionally also of the fourth space.

FIG. 1 schematically illustrates an example granulator according to the invention in a view from the side. In the figures, L indicates the length, H indicates the height and W indicates the width. In FIG. 1, the nozzles (17) are shown only in granulator compartment (A), they are typically also provided in compartment (B). The two nozzles (17A, 17B) are spaced apart in the length direction. Each nozzle in fact indicates a plurality of nozzles. In preferred embodiments, the nozzles are arranged on lines over the width of the granulator, which lines are spaced apart in the length direction. The header (12) extends in length direction in the third space (23) (as shown) and for example includes arms in the width direction for each line of nozzles, the arms are provided with rises for each individual nozzle. In alternative embodiments, the nozzles are arranged on multiple lines in the length direction, the lines being spaced apart in the width direction, and the header comprises a plurality of arms, each arm extending in the length direction and being connected by the risers to the nozzles of one such line, and the arms being spaced apart in the width direction. In still other embodiments, the enclosure of the third space (23) is provided with numerous openings for granulation liquid (10) spaced apart in the length direction, and the header comprises of a plurality of arms extending in the width direction.

FIG. 1 provides an example of the preferred embodiment wherein the header (12) is vertically spaced apart from the separation plate (15) in vertical direction, and the riser (13)

extends through the secondary gas opening (25) into the third space (23). Advantageously, the relatively hot secondary gas (6) surrounds the entire header (12) such that cooling of the granulation liquid (e.g. urea melt) in the header is avoided. As illustrated in FIG. 1, the header (12) is moreover preferably vertically spaced apart from the separation plate (15). Furthermore, the wall of the riser (13) is spaced apart from the wall of the secondary gas channels (20). In this way the secondary gas (6) in the secondary gas channels (20) and preferably completely surrounding the risers (12) may advantageously reducing cooling of the granulation liquid in the riser. Because numerous risers (13) are used, the heat exchanging wall area of the risers is relatively larger than for the header (12).

This arrangement of the header (12) provides the advantage that cooling of granulation liquid in the stein (and in the header and in the risers) by the cooler fluidization gas is avoided. The inlet for fluidization gas (5) and the inlet for secondary gas (6) are shown small, and are shown in the front wall (the wall parallel to the width), but can in fact each independently be a large aperture, in particular in the sidewall (parallel to the length), and in particular the sidewall of each granulation compartment can be provided with such an inlet for fluidization gas and/or secondary gas, the optional cooling compartment can e.g. have an inlet for fluidization gas in the sidewall.

FIG. 2 schematically illustrates an example granulator. In FIG. 2A, the flow of fluidization gas is schematically shown as a dashed line from inlet for fluidization gas (5), and then through the first space (21), around the secondary gas openings (25) and through the openings (16) in the fluidization plate (14) into the first space (21), in particular into the granulator compartments (A, B). The granulation liquid flows through the inlet for granulation liquid (10), through the granulation liquid supply manifold (11), including through the header (12) (which includes arms in width direction), and then through the risers (13) to the nozzle inlet (19). The flow of secondary gas is also schematically shown as dashed line from an inlet for secondary gas (6), and then through the third space (23) and through the secondary gas opening (25), through the secondary gas channels (20) to the nozzle inlet (19) for granulation liquid. The header (12) is arranged at the top of the third space (23), directly below the separation plate (15), but the secondary gas can flow around the header into the secondary gas channels (20).

FIG. 2A provides an example of the preferred feature that the granulation liquid header (12) is provided in the third space (23) (in particular, that the header is entirely arranged inside the third space), and the enclosure of the third space comprises the inlet for granulation liquid (10). This preferred feature is also shown in FIG. 1.

FIG. 2A illustrates an example of the embodiments wherein the header (12) abuts the separation plate (15), and wherein the riser (13) is joined to the header (12) at the secondary gas opening (25). In this embodiment, the header (12) is close to the separation plate (15), which is not preferred because the fluidization gas is often colder than the secondary gas. In particular some vertical spacing between the header (12) and the separation plate (15) is preferred (as is shown in FIG. 1).

FIG. 2B is an enlarged view perpendicular to the length of a portion of the granulator of FIG. 2A showing how the risers are joined to the header at the secondary gas opening.

FIG. 3 schematically illustrates an example of the preferred feature that the granulator comprises one or more optional cooling compartments (C). In this cooling compartment the fluidization plate (14) is for example a horizontal plate but preferably is inclined downward in the direction to the granulate outlet (7), illustrated as plate (14A). The plate (14) for example has a bend (angle) downward to the outlet (7), illustrated as alternative plate configuration (14B). Fluidization is supplied into the cooling compartment (C), in particular into the first space (21) thereof, through the openings (16) in the plate (14). The slope of the fluidization plate (14) provides the advantage the bed height increases, thereby increasing bed volume and giving advantageously a larger residence time.

Furthermore, in FIG. 3, the granulation liquid is supplied through a fourth space (24), which is an optional feature independent of the cooling compartment (C). This fourth space (24) is provided by the optional second separation plate (24A) which has openings for the bottom end of the riser (13) or through which the risers extend. The fourth space (24) provides for a simple implementation of the header (12) and for distributing the liquid to the risers. However, the longer residence time of the urea liquid in fourth space (24) may cause an increase of biuret formation which is not desirable.

Accordingly, FIG. 3 illustrates an example of the embodiment wherein the separation plate (15) between the second space and the third space is a first separation plate, and wherein the granulator further comprises a second separate plate (24A) between the first separation plate (15) and the lower wall (3). In this way the third space is provided between the first separation plate and the optional second separation plate (24A), and a fourth space (24) is provided between the second separation plate (24A) and the lower wall. The fourth space has an enclosure, and this enclosure comprises the inlet (10) for granulation liquid. The second separation plate (24A) comprises openings (24B) through which the risers (13) extend. In this way the fourth space is connected by openings (24B) with the nozzle inlet (19) for granulation liquid, and accordingly the fourth space provides the granulation liquid header (12).

FIG. 3 furthermore illustrates an example of the independently preferred feature that the granulator further comprises one or more cooling compartments. In FIG. 3, the cooling compartment is downstream of the granulation compartments and comprises the granulate outlet. The fluidization plate of the granulation compartments is a first fluidization plate and the cooling compartment comprises an upper wall and a second fluidization plate. The upper wall and the fluidization plate define a cooling first space between them. The granulator is configured for maintaining a fluidized bed of particles in said cooling first space in operation. The second fluidization plate is hence provided with numerous openings and thereby allows for passage of fluidization gas from second space (22) into the cooling first space. At least a part of the second fluidization plate is lower than said first fluidization plate, e.g. the second fluidization plate comprises a downward slope and/or downward bends. Preferably no separation plate (15) is arranged below the second fluidization plate, thereby providing space for such slope or bend.

Figure 4:
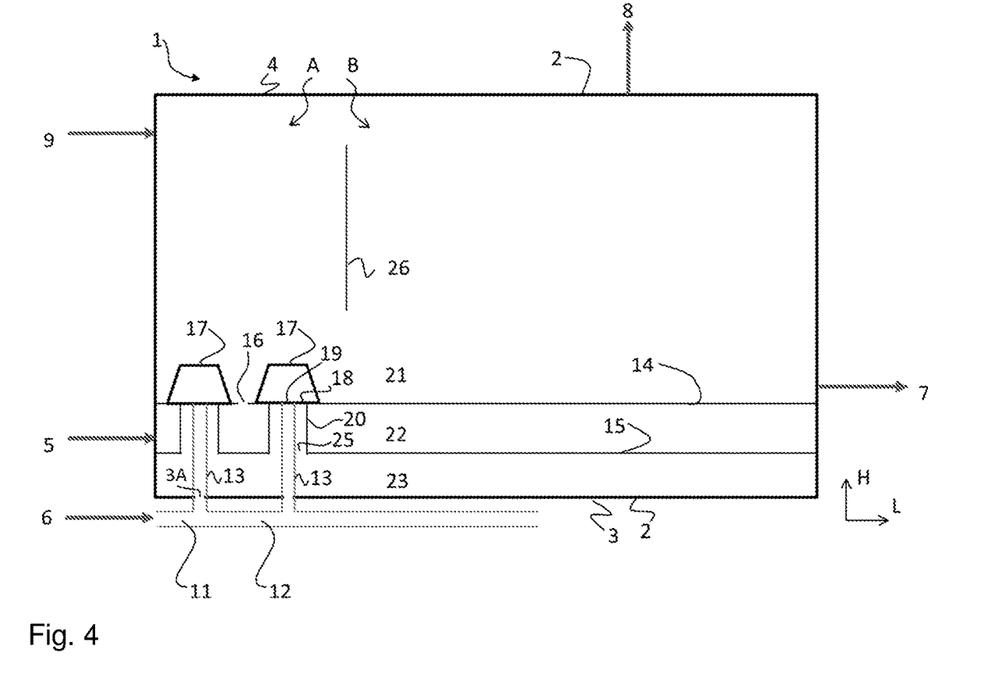
FIG. 4 schematically illustrates an example granulator according to some embodiments of the invention.

FIG. 4 schematically shows an example of an embodiment wherein the header (12) is arranged below the lower wall (3) and wherein each riser (13) extends through an opening (3A) in the lower wall (3). Hence, the risers (13) have a bottom opening at the openings (3A) or extend through these openings (3A). This provide for a simple construction. However, thermal insulation of header (12) is may be less than in to FIGS. 1, 2 and 3.

Accordingly, FIG. 4 illustrates an example of an embodiment wherein the granulation liquid header (12) is provided outside the granulator enclosure (2), and wherein the risers (13) extend (vertically) through the secondary gas openings (25), through the third space (23) and through openings (3A) for the risers (13) in the enclosure of the third space. The openings (3A) are typically provided in granulator enclosure (2). Preferably the openings (3A) are provided in the lower wall (3). This arrangement advantageously provides for good access in the third space and for access to the header.

Figure 5:
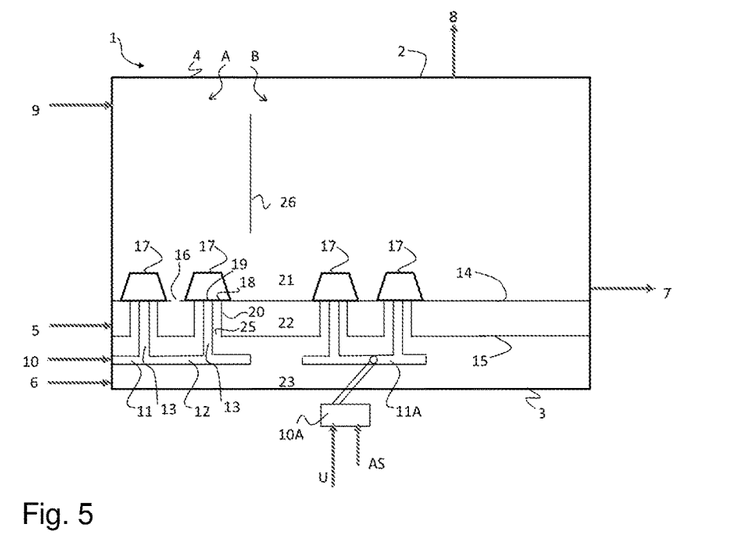
FIG. 5 schematically illustrates an example granulator according to the invention.

FIG. 5 schematically shows an example of the embodiment wherein the first granulator compartment (A) has a first granulation liquid supply manifold (11) for a first granulation liquid and the second granulator compartment (B) has a second, different, granulation liquid supply manifold (11A) which can be used for spraying a second granulation liquid with a different composition. The first granulation liquid is for example urea (comprising e.g. less than 1.0 wt. % of ammonium salts, or less than 0.10 wt. % ammonium salts). The second granulation liquid supply manifold (11A) has a dedicated inlet for granulation liquid, for instance with a mixing unit (10A) for mixing urea melt (U) or other kind of granulation liquid with a second stream. The second stream comprises for example one or more selected from the group consisting of ammonium salts, additives, micronutrients, sulphates, phosphates and nitrates. The second stream is for instance urea ammonium sulphate (UAS) with e.g. 10-50 wt. % ammonium sulphate. The second granulation liquid is for instance a urea ammonium salt melt, such as urea ammonium nitrate or urea ammonium sulfate (comprising e.g. at least 10 wt. % of the ammonium salt), preferably wherein the first liquid is for instance a urea melt.

In principle any granulation compartment can be provided with such a mixing unit. Preferably the granulation liquid supply manifolds, more preferably the mixing units, or at least some of them, have a dosing unit, such as a control valve, for precisely regulating the flow rate of additive. In a particularly preferred embodiment, the granulator comprises at least two compartments, an upstream first compartment and downstream thereof (for particles) a second compartment, having separate supply manifolds, and the supply manifold of the first compartment comprises a mixing unit. This can be used to provide e.g. a higher concentration of a component, such as an additive (e.g. an ammonium salt) in the liquid sprayed in the first compartment compared to the liquid sprayed by the nozzles in the second compartment. In this way the outer granule layers may have a higher concentration of urea. This distribution can provide for a higher critical relative humidity of the formed granules.

FIG. 5 illustrates an example of the embodiment wherein the granulator comprises a plurality of granulation liquid manifolds, each having an inlet for granulation liquid. The manifolds comprise each a header and risers. Preferably at least two granulation compartments have a different one of the granulation liquid manifolds. Preferably the granulator comprises at least two manifolds which are not connected to, or provided in, the same granulator comportment. In a preferred embodiment, the granulator comprises a first and a second granulation compartment, and the first granulation compartment comprises said first granulation liquid manifold and does not comprise said second granulation liquid manifold, and wherein a second granulation compartment comprises said second granulation liquid manifold and does not comprise said first granulation liquid manifold. Preferably, each manifold is connected to a different granulation compartment. Preferably each granulation compartment is connected to a different manifold. For example, the granulator comprises a granulation liquid manifold that is dedicated to one granulation compartment, and the nozzles of that compartment are not connected to another granulation liquid manifold. Advantageously, the different granulation liquid manifolds can use the same third space (23) for the supply of secondary gas and can use the same secondary gas. This provides for a simple design of the secondary gas supply even if different granulation liquids are used. However, the third space (23) can also advantageously be divided in compartments, each compartment having a separate inlet for secondary gas.

The granulator preferably comprises a granulation liquid supply line connected to at least one but not all of the preferred plurality of granulation liquid manifolds, and an additive feed mixer connected to the granulation liquid supply line for mixing an additive to granulation liquid in the supply line.

Figure 6A:
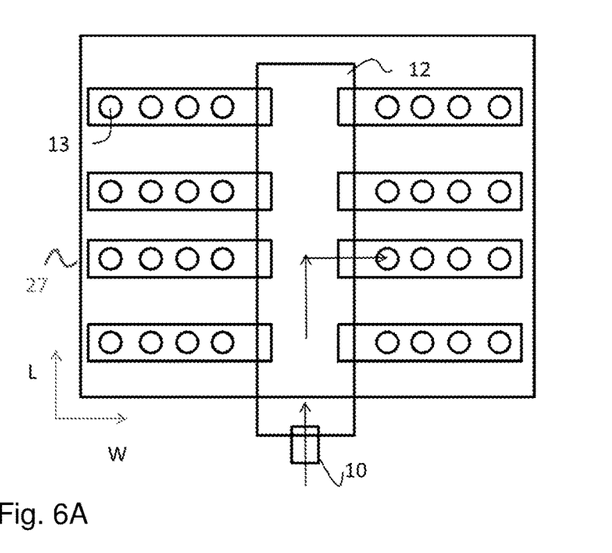
FIG. 6A—illustrates a granulator according to the invention.
Figure 6B:
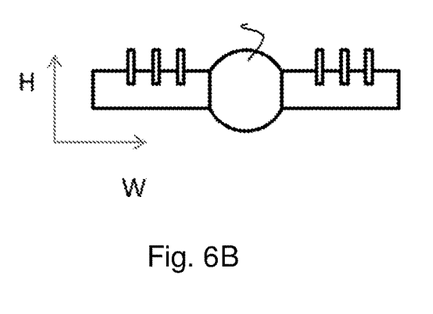
FIGS. 6B and 6C show cross-sections.
Figure 6C:
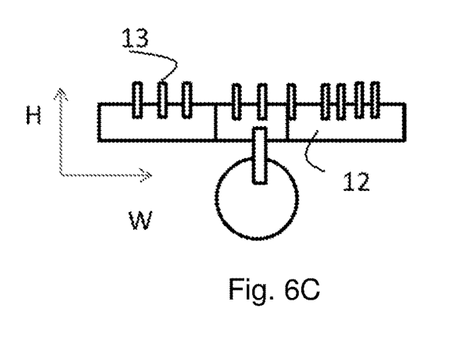

FIG. 6 schematically illustrates a top view (in the length L and width direction W) of an example granulator according to the invention (FIG. 6A) and a front view in the height direction H and the width direction W of a first embodiment (FIG. 6B) and a second embodiment (FIG. 6C). In a preferred embodiment of the invention, the header (12) includes for example a stem and arms which are provided inside the enclosure (2). The stem runs in the length direction and in the middle of the granulator in the width direction. An example is shown in FIG. 6A. The arms extend in the width direction at opposed sides of the stem, optionally at both sides above the stem (FIG. 6C). In this way advantageously a short residence time of the granulation liquid is achieved (in terms of a short average path for the granulation liquid between the inlet (10) and the riser (13), and hence to the nozzle inlets (19). A short residence time and short average flow path are in particular advantageous to avoid or reduce biuret formation in case urea is the granulation liquid. Biuret formation occurs rapidly in hot concentrated urea solutions at high temperature. In particular the arrangement of the header below the separation plate (15) allows for the advantageous configuration of FIG. 6A.

Figure 7:
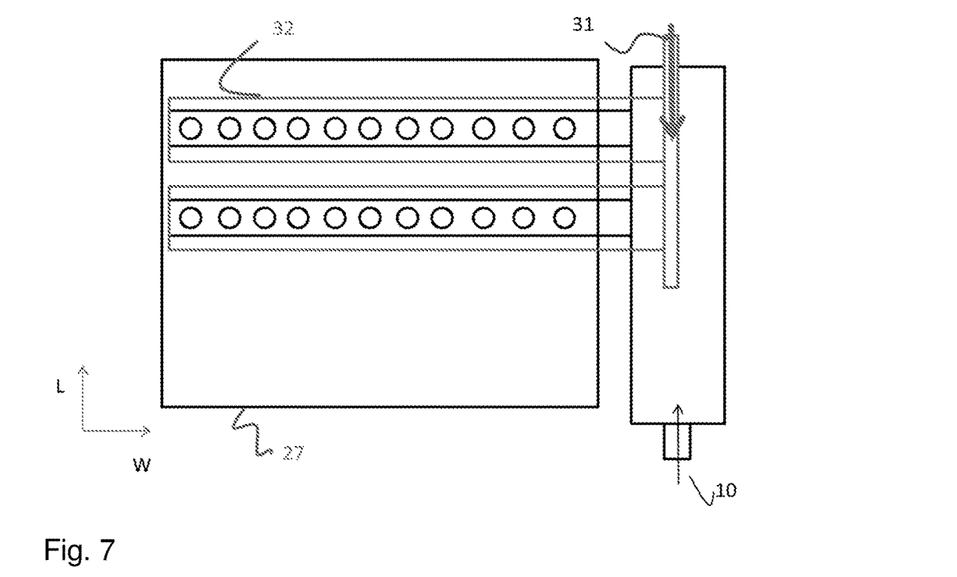
FIG. 7 schematically illustrates a reference granulator, not according to the invention.

FIG. 7 illustrates a reference granulator not according to the invention, wherein an enveloping tray (32) is used for the supply of secondary gas from an inlet (31). As an independent feature, the stem of the header runs outside the granulator enclosure (2), on one side of the granulator, in the length direction and the stem is provided with arms extending in the width direction on one side. The arms extend for instance in the space inside the granulator enclosure directly below the fluidization plate. These arms are provided with the risers. In FIG. 7, the arms with the enveloping trays (32) are for example arranged directly below the fluidization plate. If the reference granulator of FIG. 7 is modified by replacing the enveloping tray (32) by secondary gas channels according to the invention, the modified FIG. 7 illustrates an embodiment of the granulator of the invention which is less preferred than the embodiment of FIG. 6A because the average flow path length for the granulation liquid is shorter in FIG. 6A.

FIG. 8 shows an isometric view of an example granulator according to the invention. The side walls (27) are shown; in the illustrated example one sidewall includes a gap for inlet for fluidization gas (5) as well as a gap for inlet for secondary gas (6). The header (12) is arranged inside the third space (23), similarly to FIG. 1.

In a preferred embodiment (an example of which is illustrated in FIG. 8), the header (12) is connected to a feed channel for cleaning fluid (such as water and/or steam). For example, the header, more in particular the granulation liquid inlet (10), is connected to a cleaning supply line (28) which supply line is connected, preferably through a valve, to the feed channel. The feed channel is for instance a steam inlet (29). The header preferably also has an inlet connected (preferably through a valve, and for instance through cleaning supply line (28)) to a drying gas supply channel, which is preferably for drying air, e.g. to a gas supply channel (30). The gas supply channel (30) is for instance in turn connected to an outlet for secondary gas (e.g. secondary air) of the second space (22). Alternatively, the gas supply channel (30) can be to any gas supply, such as to a duct for secondary gas (6) or to the first space (21) to receive inlet for fluidization gas from inlet (5) or to some other duct for fluidization gas. The connections are e.g. independently provided by a three-way valve or e.g. comprise a T-joint with valves. In this way, the granulator can be switched between a first configuration wherein the header (12) receives only granulation liquid, a second configuration wherein the header (12) receives only cleaning fluid (e.g. steam), and a third configuration wherein the header (12) receives only secondary gas from inlet (6). In this way, the granulation liquid supply manifold (11) including the header (12) and the riser (13) can be flushed firstly with a cleaning fluid (e.g. water and/or steam) and secondly be dried using a drying gas (e.g. the secondary gas) thereby cleaning the granulation liquid supply manifold (11). In some embodiments, the gas supply channel (30) and the cleaning supply line (28) for instance have separate connections to the header.

The invention also pertains to a urea plant comprising the fluidized bed granulator as described. The urea plant comprises in addition e.g. a high pressure urea synthesis section operating at a pressure of at least 100 bar (e.g. at 110-160 bar), a recovery section including a low pressure recovery section (e.g. 1-10 bar) and optionally a medium pressure recovery section (operating e.g. at 15-60 bar) arranged between the synthesis section and the low pressure recovery section, and an evaporation section downstream of the recovery section for evaporating water from the urea solution to give a urea melt. The granulation liquid supply manifold of the granulator is connected to an outlet for urea melt of the evaporation section. The high pressure synthesis section comprises for instance a high pressure reactor, a high pressure stripper (e.g. using $CO_2$ as strip gas, or using thermal stripping) and a high pressure carbamate condenser, e.g. arranged in an isobaric loop. The stripper has an outlet to the recovery section. The urea formation reaction is based on the reaction of $NH_3$ and $CO_2$ at high pressure to ammonium carbamate and dehydration thereof to urea and water. The evaporation section comprises e.g. one or more (vacuum) evaporation stages in series, and operates e.g. at a pressure below 1 bar absolute. In the recovery section(s), the urea solution is e.g. subjected to heating so as to decompose ammonium carbamate and to remove ammonia from the urea solution, thereby purifying the urea solution. The removed gaseous ammonia and $CO_2$ are recycled to the synthesis section after condensation.

The invention also pertains to a granulation method, preferably of urea, carried out in the granulator as described, and more preferably in a urea plant as described. The method comprises for example supplying granulation liquid, e.g. as described, preferably a urea melt, to the inlet for granulation liquid (10) and through the granulation liquid supply manifold (11) including the header (12) and the risers (13), supplying fluidization gas to the inlet for fluidization gas (5) and supplying secondary gas to the inlet for secondary gas (6) of the granulator, and withdrawing granulate from the granulate outlet (7), with the gases preferably as described. The method typically furthermore comprises maintaining a fluidized bed of granules in the first space (21) and supplying granulation liquid into the first space using the nozzles (17). The nozzles are for example atomizing nozzles using the secondary gas to provide a spray of the granulation liquid. In a further embodiment the nozzles are for example film nozzles providing a film of the granulation liquid from a first nozzle outlet, and the secondary gas is passed through a separate outlet (e.g. a ring), surrounding the first outlet, to transport particles of the fluidized bed through said film.

The reference numerals as used throughout this description and the claims are for illustrative purposes only and to assist in understanding the drawings. These reference numerals do not limit the claims and the invention. The skilled person understands that the cooling compartment can also be used in FIGS. 1, 2, 4, 5, 6 and 8, optionally including the inclined fluidization plate and/or inclined separation plate. The use of two or more granulation liquid manifolds and a mixing unit is also possible at least in FIGS. 1, 2, 3, 4, 6 and 8. The side wall design of FIG. 8 can also be used at least with FIGS. 1, 2, 3, 5 and 6.

The invention claimed is:

1. A fluidized bed granulator for granulation with urea or urea-containing liquids, the granulator comprising a granulator enclosure, wherein the granulator enclosure comprises: a lower wall, an upper wall, an inlet for fluidization gas, an inlet for secondary gas, an outlet for solid product particles, an outlet for exhaust gas, and optionally an inlet for seed particles, wherein the granulator enclosure comprises a plurality of granulation compartments, which are arranged in series in a length direction of the granulator, wherein the granulator further comprises an inlet for granulation liquid and a granulation liquid supply manifold, wherein the granulation liquid supply manifold comprises a granulation liquid header and a plurality of risers, wherein the granulation liquid header is connected to said inlet for granulation liquid and to a plurality of said risers, wherein the granulator enclosure further comprises a fluidization plate and at least in said granulation compartments a separation plate, wherein the separation plate is spaced apart from the fluidization plate in vertical direction and is placed below the fluidization plate, wherein the separation plate is arranged between said lower wall and said fluidization plate, wherein said granulator enclosure comprises a first space between said upper wall and said fluidization plate, a second space between said fluidization plate and said separation plate, and a third space between said separation plate and said lower wall, said first, second and third space each having an enclosure, wherein said granulator is configured for holding a fluidized bed of particles in operation in said first space, and wherein the enclosure of said first space comprises said outlet for solid product particles, said outlet for exhaust gas, and optionally said inlet for seed particles, wherein the enclosure of said second space comprises said inlet for fluidization gas, and wherein the fluidization plate comprises openings for passage of said fluidization gas from said second space to said first space, wherein said enclosure of said third space comprises said inlet for secondary gas, wherein the granulator comprises in said granulator compartments a plurality of nozzles for supplying said granulation liquid into said first space, wherein at least one of said nozzles comprises a nozzle inlet for said secondary gas and a nozzle inlet for said granulation liquid, wherein said granulator comprises a secondary gas channel which extends from a secondary gas opening in said separation plate through said second space to said nozzle inlet for secondary gas, wherein said granulation liquid supply manifold is in part provided in said third space and in part in said second space and wherein at least one of said risers is at least in part provided inside said secondary gas channel, wherein said riser passes through said secondary gas opening or is joined to said header at said secondary gas opening.

2. A granulator according to claim 1, wherein said secondary gas channel is a first tube and said riser or part of said riser that is provided in said secondary gas channel is a second tube, wherein said first tube surrounds said second tube in a cross-section in the horizontal plane for at least one vertical position.

3. A granulator according to claim 1, wherein said granulation liquid header is provided in said third space and said enclosure of said third space comprises said inlet for granulation liquid.

4. A granulator according to claim 3, wherein said granulation liquid header is spaced apart from said separation plate in vertical direction, and wherein said riser extends through said secondary gas opening in said separation plate.

5. A granulator according to claim 3, wherein said granulation liquid header comprises a stem and branches, wherein said stem extends in the length direction of the granulator, wherein said branches extend in the width direction of the granulator outwardly from said stem at opposed sides of said stem, said sides being opposite in the width direction, such that said stem is provided substantially in the center in width direction of said third space, and wherein said branches are each connected to a plurality of said risers.

6. A granulator according to claim 1, wherein said separation plate between said second and third space is a first separation plate, wherein said granulator further comprises a second separate plate between said first separation plate and said lower wall, wherein said third space is provided between said first and second separation plate, wherein a fourth space is provided between said second separation plate and said lower wall, said fourth space having an enclosure, said enclosure of said fourth space comprising said inlet for granulation liquid, wherein said second separation plate comprises an opening through which one of said risers extends, thereby connecting said fourth space with said nozzle inlet for granulation liquid, such that said fourth space provides said granulation liquid header.

7. A granulator according to claim 1, wherein the riser and the secondary gas channels are concentric tubes.

8. A granulator according to claim 1, wherein said granulator further comprises one or more cooling compartments downstream of said granulation compartments, wherein said fluidization plate of said granulation compartments is a first fluidization plate, wherein at least one said cooling compartments comprises an upper wall and a second fluidization plate, wherein said upper wall and said second fluidization plate define a cooling first space between them, wherein the granulator is configured for maintaining a fluidized bed of particles in said cooling first space in operation, and wherein said second fluidization plate is at least in part lower than said first fluidization plate.

9. A granulator according to claim 8, wherein said second fluidization plate comprises a downward slope in the length direction, optionally with a bend.

10. A granulator according to claim 1, wherein said granulator comprises a first and a second granulation liquid manifold, each manifold having an inlet for granulation liquid, and each comprising a header and risers, wherein at a first granulation compartment comprises said first granulation liquid manifold and does not comprise said second granulation liquid manifold, and wherein a second granulation compartment comprises said second granulation liquid manifold and does not comprise said first granulation liquid manifold.

11. A granulator according to claim 10, wherein the granulator further comprises an granulation liquid supply line connected to at least one but not all of said granulation liquid manifolds, and an additive feed mixer connected to said granulation liquid supply line for mixing an additive to the granulation liquid in said supply line.

12. A granulator according to claim 1, wherein said the header has an inlet connected, preferably through a valve, to a feed channel for a cleaning fluid and an inlet connected, preferably through a valve, to a gas supply channel that is connected to an outlet of the second space.

13. A granulator according to claim 1 wherein said granulator comprises at least one divider dividing said first space into zones, wherein said zones define said granulation compartments.

14. A urea granulation method, carried out in the granulator according to claim 1, wherein the method comprises supplying urea melt as granulation liquid to the inlet for granulation liquid and through the granulation liquid supply manifold including the header and the risers, supplying fluidization gas to the inlet for fluidization gas and supplying secondary gas to the inlet for secondary gas of the granulator, and withdrawing granulate from the granulate outlet, and maintaining a fluidized bed of granules in the first space and supplying granulation liquid into the first space using the nozzle.

* * * * *